United States Patent
Inoue

(10) Patent No.: US 7,692,152 B2
(45) Date of Patent: Apr. 6, 2010

(54) RADIATION DETECTING APPARATUS, SCINTILLATOR PANEL, RADIATION DETECTING SYSTEM, AND METHOD FOR PRODUCING SCINTILLATOR LAYER

(75) Inventor: Masato Inoue, Kumagaya (JP)

(73) Assignee: Canon Kabushiki Kaisha, Tokyo (JP)

( * ) Notice: Subject to any disclaimer, the term of this patent is extended or adjusted under 35 U.S.C. 154(b) by 401 days.

(21) Appl. No.: 11/680,746

(22) Filed: Mar. 1, 2007

(65) Prior Publication Data

US 2007/0205371 A1 Sep. 6, 2007

(30) Foreign Application Priority Data

Mar. 2, 2006 (JP) ............................. 2006-056473

(51) Int. Cl.
 *G01T 1/20* (2006.01)
 *G01T 1/24* (2006.01)
 *G01T 1/10* (2006.01)
(52) U.S. Cl. ................................ 250/361 R; 250/370.1; 250/458.1
(58) Field of Classification Search .................. None
 See application file for complete search history.

(56) References Cited

U.S. PATENT DOCUMENTS

| | | | | |
|---|---|---|---|---|
| 4,820,926 A * | 4/1989 | Popma et al. | ............ | 250/486.1 |
| 7,256,404 B2 | 8/2007 | Inoue et al. | ............ | 250/370.11 |
| 2006/0033031 A1 | 2/2006 | Takeda et al. | .......... | 250/370.11 |
| 2006/0033040 A1 | 2/2006 | Okada et al. | ............. | 250/484.2 |
| 2007/0131867 A1 | 6/2007 | Okada et al. | ........... | 250/370.09 |
| 2007/0237668 A1* | 10/2007 | Martins Loureiro et al. | ... | 419/48 |

FOREIGN PATENT DOCUMENTS

| | | |
|---|---|---|
| WO | WO 98/36290 | 8/1998 |
| WO | WO 99/66350 | 12/1999 |

OTHER PUBLICATIONS

Thomas P. Flanagan, "Re-evaluating hot melt adhesives." Adhesives Age, vol. 9, No. 3, pp. 28- 31 (Mar. 1966).

* cited by examiner

*Primary Examiner*—David P Porta
*Assistant Examiner*—Carolyn Igyarto
(74) *Attorney, Agent, or Firm*—Fitzpatrick, Cella, Harper & Scinto

(57) ABSTRACT

A radiation detecting apparatus includes: a sensor panel that has a substrate, and has a plurality of pixels each of which has a photoelectric conversion element for converting light into an electric signal, arranged on the substrate; and a scintillator layer arranged on a reverse side of the pixels with respect to the substrate, wherein the scintillator layer contains an activator added in a main ingredient, and has a higher concentration of the activator in a peripheral area than in a center area, in a surface direction of the scintillator layer.

6 Claims, 7 Drawing Sheets

RADIATION DETECTING APPARATUS, SCINTILLATOR PANEL, RADIATION DETECTING SYSTEM, AND METHOD FOR PRODUCING SCINTILLATOR LAYER

BACKGROUND OF THE INVENTION

1. Field of the Invention

The present invention relates to a radiation detecting apparatus, a scintillator panel, a radiation detecting system, and a method for forming a scintillator layer by deposition; and particularly relates to the scintillator panel, the radiation detecting apparatus, the radioactive rays detection system, which are used in radiographing used in medical diagnosis equipment and non-destructive inspection equipment, and the method for forming a scintillator layer by deposition. In the present specification, "radiation" shall include corpuscular rays such as X-rays, gamma-rays, and alpha-particles and beta-particles. In addition, the "scintillator" shall be a device that converts incident radiation such as X-rays and gamma-rays to light having a wavelength range that can be sensed by a photoelectric conversion element.

2. Description of the Related Art

A radiation detecting apparatus conventionally used in general radiographing uses a radio-sensitized paper having a scintillator layer which converts X-rays into light, and a radiation film having a photosensitive layer.

However, a digital radiation detecting apparatus has been recently developed which has a scintillator layer and a two-dimensional photodetector including photoelectric conversion elements. The digital radiation detecting apparatus facilitates image processing because the obtained data is digital and the data can be shared among multiple persons, when the data is taken into a networked computer system. In addition, if the image digital data is saved in a magneto-optical disk or the like, the digital radiation detecting apparatus can remarkably reduce the storage space required, compared to the case of saving image data in a film, and has an advantage of facilitating a search for past images. In addition, the digital radiation detecting apparatus can reduce the dosage of exposure to radiation for the patient, because a digital radiation detecting apparatus having characteristics of high sensitivity and high sharpness has been proposed along with the progress of the apparatus.

For instance, International Publication Number WO 98/036290 discloses a digital radiation detecting apparatus that has a scintillator layer which is produced with a vacuum deposition technique and includes crystals of cesium iodide (hereafter referred to as CsI) grown into a columnar shape, connected with a photodetector directly or through a protection film. A thus configured digital radiation detecting apparatus can be made with improved sensitivity and sharpness in comparison with that provided with a scintillator layer having conventional scintillators made of granular crystals assembled together.

In addition, International Publication Number WO 99/066350 discloses a digital radiation detecting apparatus having a configuration of adhesively bonding a CsI surface of a scintillator prepared, for instance, by vapor-depositing CsI on a base plate, to a photodetector (which is not shown in the drawings).

A columnar crystal of CsI or the like, which forms a scintillator layer, has properties of absorbing external moisture and deliquescing. A scintillator layer having absorbed moisture deteriorates in its light emission properties and sharpness. For this reason, the above-described conventional radiation detecting apparatus or scintillator panel has a moisture proof protective film for preventing the entry of external moisture.

In addition, a radiation detecting apparatus disclosed in U.S. Pat. No. 4,820,926 has an outermost layer containing only the activator of Tl formed on a light emission material layer.

However, it has been demanded to further improve a moisture-proof effect. Particularly, radiation detecting apparatus for use in a hostile environment like a high-temperature and high-humidity environment has been required to have an improved moisture-proof effect.

SUMMARY OF THE INVENTION

Accordingly, an object of the present invention is to provide a radiation detecting apparatus and a scintillator panel which have a higher moisture-proof effect than ever before, and a method for producing a scintillator layer having a sufficient moisture proof function.

A radiation detecting apparatus according to the present invention has: a sensor panel that has a substrate, and has a plurality of pixels each of which has a photoelectric conversion element for converting light into an electric signal, arranged on the substrate; and a scintillator layer arranged over the pixels, wherein the scintillator layer contains an activator and a main ingredient, and has a higher concentration of the activator in a peripheral area than in a center area, in a surface direction of the scintillator layer.

In addition, a scintillator panel according to the present invention has: a substrate; and a scintillator layer arranged on the substrate, wherein the scintillator layer contains an activator added in a main ingredient and has a higher concentration of the activator in a peripheral area than in a center area, in a surface direction of the scintillator layer.

A method for producing a scintillator layer according to the present invention includes: arranging a vapor deposition boat for a main ingredient of the scintillator layer and a vapor deposition boat for an activator in a vacuum chamber so as to face to a substrate on which the scintillator layer is to be deposited; arranging the vapor deposition boat for an activator at such a position as to face to a peripheral area of the substrate; and conducting a vapor-depositing operation.

The present invention can provide a radiation detecting apparatus and a scintillator panel which inhibit the diffusion of moisture in a peripheral area of a scintillator layer, and have a sufficient moisture proof function; and a method for producing the scintillator layer having the sufficient moisture proof function.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

DESCRIPTION OF THE EMBODIMENTS

In the next place, the best modes for carrying out the present invention will be described in detail with reference to the drawings.

First Embodiment

Figure 1:
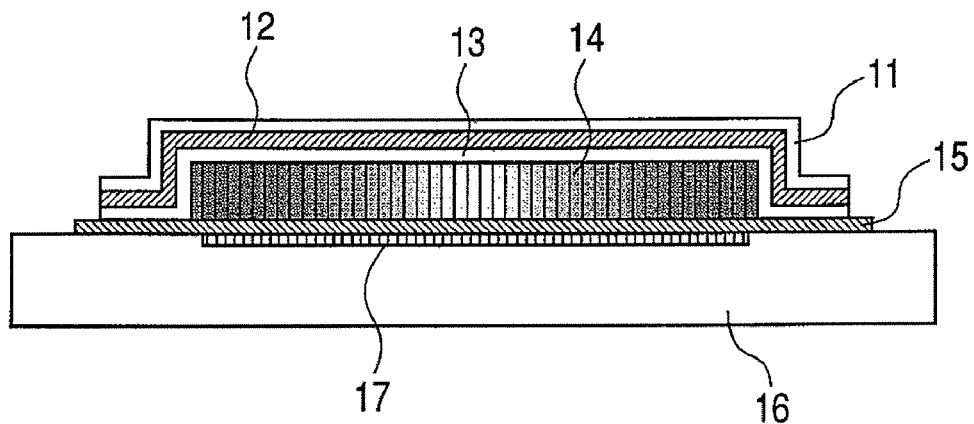
FIG. 1 shows a sectional view of a radiation detecting apparatus according to the first embodiment of the present invention.

FIG. 1 shows a sectional view of a radiation detecting apparatus according to the first embodiment of the present invention. In FIG. 1, reference numeral 11 denotes a polyethylene terephthalate resin layer which is a support for an electromagnetic shield layer 12, and reference numeral 12 denotes an aluminum layer which functions as an electromagnetic shield body, and has a light reflection function and a moisture-proof function.

In FIG. 1, reference numeral 13 denotes a polyolefin-based hot-melt adhesive resin layer which is a thermoplastic resin layer having an adhesively bonding function and a moisture-proof function, reference numeral 14 denotes a scintillator layer including columnar crystals, reference numeral 15 denotes an insulation layer, and reference numeral 16 denotes a glass substrate. In addition, reference numeral 17 denotes a photoelectric conversion element array in which pixels including a photosensor and a TFT using amorphous silicon are arrayed into a two-dimensional form.

Figure 2A:
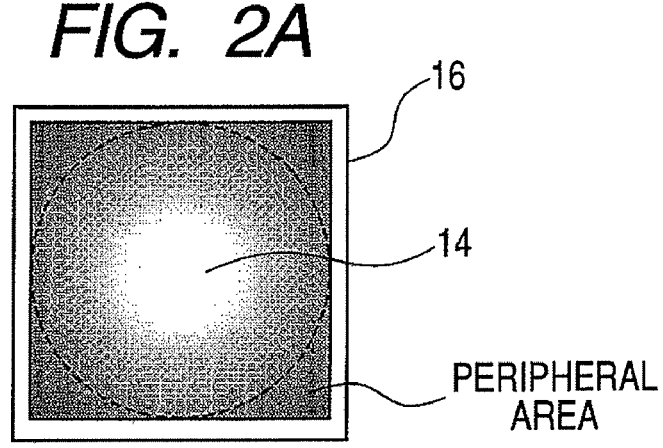
FIG. 2A is a plan view showing the Tl concentration in a scintillator layer of a radiation detecting apparatus according to the first embodiment of the present invention.
Figure 2B:
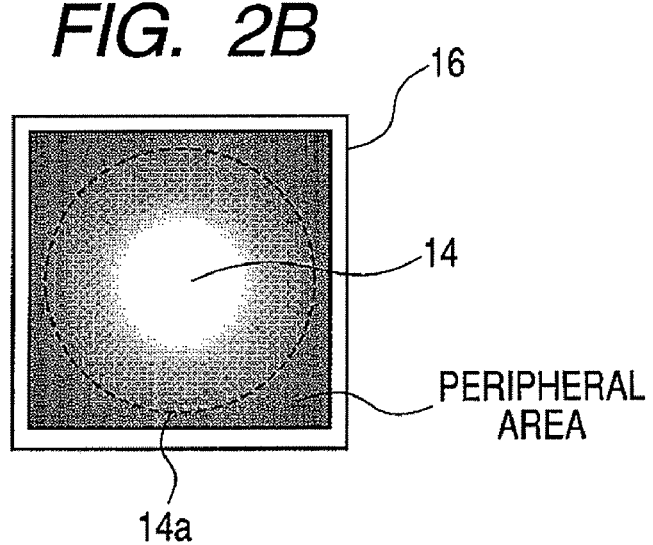
FIG. 2B is a plan view showing the Tl concentration in a scintillator layer of a radiation detecting apparatus according to the first embodiment of the present invention.

In FIG. 1, a scintillator layer 14 including columnar crystals is made from CsI as a main ingredient and Tl which is added as an activator. In FIG. 1, as shown in the scintillator layer 14, the variation of the concentration of added Tl among the pixels is shown by a gray level using black and white. A black part in a peripheral area shows where Tl exists in high concentration, and as is clear from the figure, the concentration of Tl gradually increases from a central part to the peripheral area. FIGS. 2A and 2B are two-dimensional views showing the distribution of the Tl concentration when viewed from above. It is understood from the figures that the concentration of Tl generally concentrically and isotropically changes from the center of the scintillator layer 14 to the peripheral area on a glass substrate 16. The dashed line means that the Tl concentration is particularly high in the peripheral area outside the line. FIG. 2A shows an example in which the Tl concentration is particularly high in four corners of the square glass substrate, and FIG. 2B shows an example in which the Tl concentration is high even in more inward parts. The Tl concentration in the peripheral area does not need to be all uniform, but may be higher in a part of the peripheral area than in other parts, as needed. For instance, when a wire is drawn out from a photoelectric conversion element array in a region 14a, in a configuration in FIG. 2B, irregularities may be formed in an insulation layer 15 by the wire, and facilitate moisture to enter the inner part through an interface between the insulation layer 15 and the protection film 13. In such a case, the moisture durability of the scintillator layer 14 can be improved by making the Tl concentration in the region 14a higher than that in the other peripheral areas. When it is a problem that moisture enters from only one part of the peripheral area, it is also acceptable to make the Tl concentration higher only in that part, while making the Tl concentration in all other parts equal to that in the central part.

It is considered that the moisture enters into the scintillator layer 14 from the perimeter of the scintillator layer 14. In other words, it is considered that the moisture enters from an interface between the hot melt adhesive resin layer 13 that serves as the moisture proof protective film and a member (insulation layer) which directly contacts with the hot melt adhesive resin layer 13, gradually invades the inner part, and diffuses toward the central part from a circumferential part (peripheral area) of the scintillator layer 14. In the present embodiment, the scintillator layer 14 can prevent its peripheral area from deliquescing even when the moisture has invaded into the scintillator layer 14, and further inhibit moisture from diffusing into the center area, by making the Tl concentration in the peripheral area higher than that in the center area.

In the next place, a method for adding Tl will be described. It has been elucidated from an experiment that a Tl concentration for making the scintillator layer 14 emit more light can be in a range shown by the following expression, due to properties of CsI, when the concentration of CsI containing Tl is determined as 100 [mol %]:

CsI(Tl): Tl=100:0.5 to 2.0 [mol %]

Figure 3:
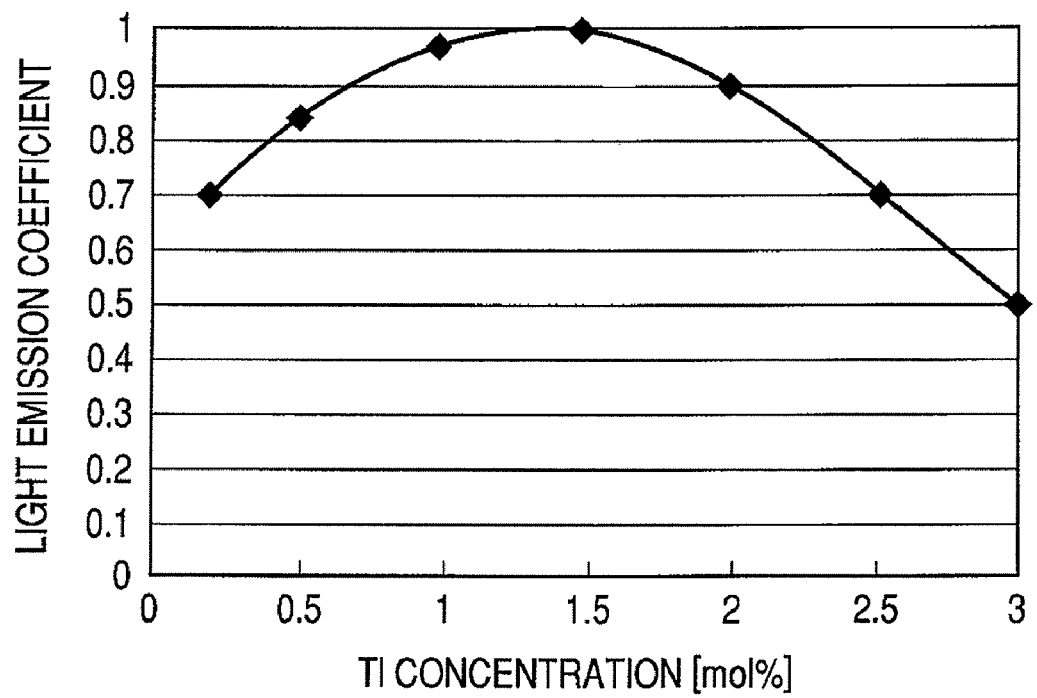
FIG. 3 is a characteristic view showing a relationship between Tl concentration and a light emission coefficient.

FIG. 3 is a graph showing a relationship between Tl concentration and a quantity of light emission (light emission coefficient). The light emission coefficient in FIG. 3 shows a ratio of a quantity of light emission to the maximum quantity of light emission when the maximum quantity is determined as 1. As is shown in FIG. 3, the quantity of light emission becomes maxim when the Tl concentration is about 1 to 1.5 [mol %]. However, the Tl concentration can not be determined only from the quantity of light emission, because it is known that the sharpness of the obtained image decreases with the increase of the Tl concentration.

It is also elucidated from an experiment that the Tl concentration for giving the scintillator layer 14 sufficient moisture-proof effects, namely, for effectively inhibiting moisture from diffusing can be in such a range as to satisfy the following expression:

CsI(Tl): Tl=100:1.0 [mol %] or more

Figure 4:
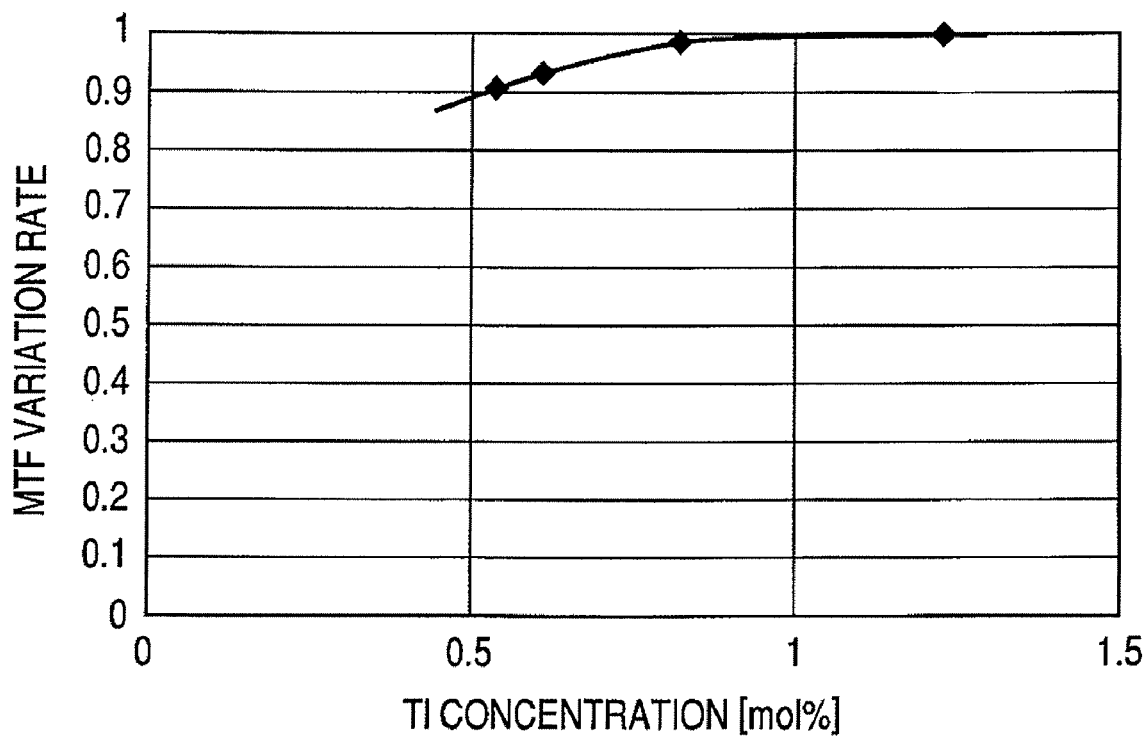
FIG. 4 is a characteristic view showing a relationship between Ti concentration and an MTF variation rate.

FIG. 4 shows a relationship between Tl concentration and a variation rate of MTF (Modulation Transfer Function). In the experiment, the variation rate of the MTF was determined by measuring the MTFs of a sample before and after having been left in an environment with humidity of 50% at 25° C. for 24 hours. As is shown in FIG. 4, the variation rate of the MTF decreases along with the increase of the Tl concentration. When the Tl concentration is 0.7 [mol %] or higher, the variation rate is little affected by deliquescence, when the Tl concentration is 1.0 [mol %] or higher, the deliquescence does not substantially cause any problem, and furthermore, when the Tl concentration exceeds 1.5 [mol %], the Tl concentration should show a sufficient protective effect even in a more severe environment. The reason why the MTF was adopted as an index of the moisture-proof effect will now be described. When a columnar crystal of CsI (Tl) absorbs moisture and deliquesces, an area of the surface from which the columnar crystal emits light increases, or adjacent crystals adhere to each other, and consequently the crystals emit light from almost one surface; in other words, lights emitted from the adjacent crystals are superposed. For this reason, as the columnar crystals deliquescence over a wider range, the columnar crystals in the wider range cohere with each other, and their output light beams are superimposed on each other.

Then, an image including signals detected by a sensor becomes blurred, because the sensor detects many superposed light beams (information). In other words, the MTF, which is the sharpness of the image, is decreased. The MTF is an index of the sharpness.

The MTF is measured by: firstly arranging a lead plate (or a lead plate having an aperture of slit shape) for intercepting X-rays on an incident side of the X-rays; irradiating a sensor with X-rays; determining an output of a sensor in a part intercepted by the lead plate as zero and an output of the sensor in a part not intercepted by the lead plate as 1; measuring the output of the sensor in the end of the lead plate; Fourier-transforming the output in order to know how the output varies in the vicinity of the end; and numerically expressing a degree of blurring in every spatial frequency. When the MTF is 0.5 at 21 p/mm for instance, the value means that when two pairs of information of 1 and 0 exist in one millimeter, the information changes from 1 to 0.5. In other words, it means that the information is blurred. The smaller the value of the MTF, the more difficult the judgment for the difference between 1 and 0 becomes.

As was described above, the Tl concentration in a peripheral area of a scintillator layer can be set at 1.0 [mol %] or higher, and further can be set at a concentration higher than 1.5 [mol %]. On the other hand, the Tl concentration in the inner part than the peripheral area of the scintillator layer is 0.5 [mol %] or more but 1.5 [mol %] or less, in consideration of a balance between the quantity of light emission and sharpness.

A practical method for forming a scintillator layer with a vapor deposition technique will be now described with reference to FIG. 5.

Figure 5:
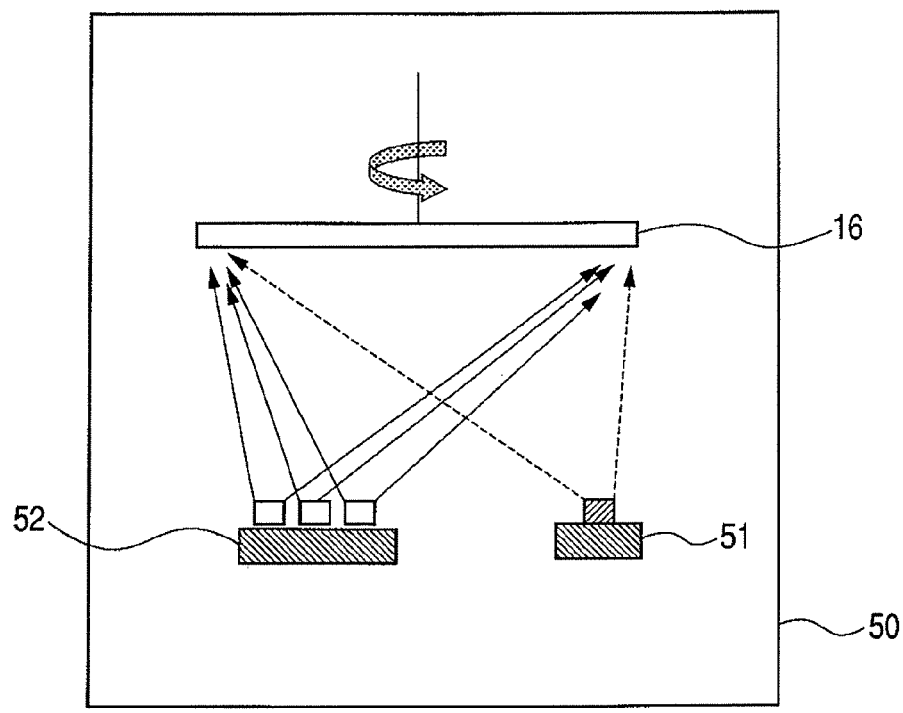
FIG. 5 is a schematic block diagram showing a vapor-deposition apparatus for forming a scintillator layer by vapor deposition.

FIG. 5 shows a vapor deposition apparatus for vapor-depositing CsI (Tl) for forming a scintillator layer. In FIG. 5, reference numeral 16 denotes a glass substrate on which a photoelectric conversion element array 17 is formed and the scintillator layer will be formed with a vapor deposition technique, reference numeral 50 denotes a vacuum tank (vacuum chamber) in the vapor deposition apparatus, reference numeral 51 denotes an evaporation boat on which TlI is placed, and reference numeral 52 denotes an evaporation boat on which CsI is placed.

An evaporation boat 51 is arranged so as to face toward a peripheral area of a glass substrate 16.

A scintillator layer having activators distributed in its plane direction by a vapor deposition method is formed, for instance, by: arranging a glass substrate 16 to be a base on a substrate holder as shown in FIG. 5 so that a surface to be vapor-deposited faces downward; arranging, for instance, many boats 52 for evaporating CsI and a boat 51 for evaporating TlI on a heat source for vapor deposition at positions shown in FIG. 5; evacuating a vacuum tank (vacuum chamber) 50 of a vapor deposition apparatus; and heating each boat by using the vapor deposition source while rotating the substrate holder around its center. Then, the vapor of CsI flies out from many boats of CsI, and deposits on the surface to be vapor-deposited (shown by an arrow of a continuous line). On the other hand, Tl which is an activator deposits in high amounts in the peripheral area of the substrate holder, and deposits in low amounts in the central part to form distribution, because Tl is supplied from one vapor deposition source and the vapor deposition source is placed at a position apart from the rotation axis of the substrate holder.

The thus obtained scintillator is subjected to activating an activator by heating the scintillator at an annealing temperature of 200° C. to 400° C. for 0.5 to 5 hours, and then is used for producing a radiation detecting apparatus. The annealing temperature must be set at such a temperature as not to affect photoelectric transfer characteristics of a photoelectric conversion element formed on a glass substrate.

In the present embodiment, as described above, the Tl concentration can be set at 1.5 [mol %] or higher in a peripheral area of a scintillator layer, and at 0.5 to 1.5 [mol %] in an inner portion than the peripheral area, in consideration of a balance between the quantity of light emission and sharpness. Then, there may be cases where the quantity of light emission in the center area is larger than that in the peripheral area, or the quantity of light emission in the peripheral area is larger than that in the center area.

In other words, when the concentration of an activator is distributed in a scintillator layer, a quantity of light emission is distributed on the surface of the scintillator layer. When it becomes a problem that the quantity of light emission varies from one portion to another, this variability of the quantity of light emission can be reduced, by annealing the scintillator layer in response to light emission quantity distribution while making use of a phenomenon that the quantity of light emission varies depending on an annealing temperature.

Figure 6:
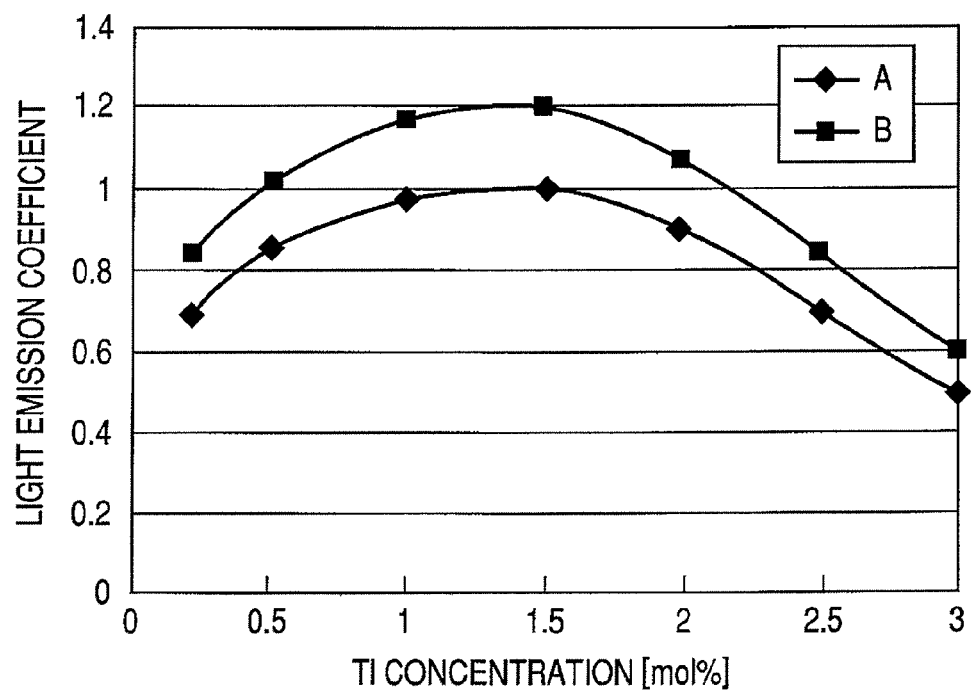
FIG. 6 is a characteristic view showing the dependency of characteristics of Tl concentration and a light emission coefficient on temperature.
Figure 12:
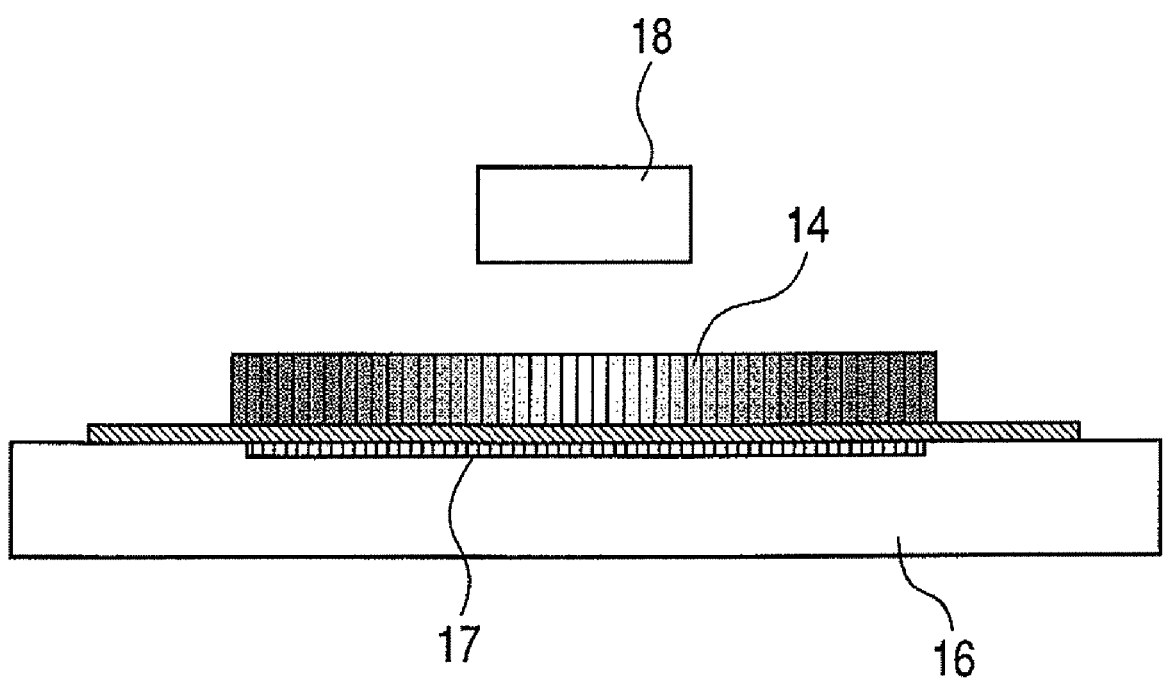
FIG. 12 is a view showing a case of having heated a scintillator layer with the use of a lamp heater.

FIG. 6 is a view showing a dependency of the quantity of light emission on an annealing temperature. In FIG. 6, the annealing temperature B is set at about 20% higher than the annealing temperature A. Then, it is clear that a scintillator layer annealed at a higher temperature is more activated by an activator and emits more light. However, after the scintillator layer is sufficiently activated, the quantity of light emission does not increase any more, so that there is naturally an upper limit in the annealing temperature. For instance, when the quantity of light emission in a center area is lower than that in a peripheral area, the quantity of light emission in the central part can be increased by setting the annealing temperature in the vicinity of the central part at a higher temperature, and the quantity of light emission in a plane of a scintillator layer can be made uniform by setting the annealing temperature so as to be distributed in an annealing environment. In order to set the annealing temperature in the center area at a higher temperature, it is recommended to arrange a heat source such as a ceramic heater, a lamp heater, and a combination of a metal plate and a sheath heater at a position facing the center area of a substrate (while not arranging such a heat source facing the peripheral area), and to heat the scintillator layer. FIG. 12 is a view showing a case of having heated a scintillator layer with the use of a lamp heater 18. Usable lamp heaters include a tungsten halogen lamp, a xenon arc lamp and a graphite heater.

Materials for a scintillator having a columnar structure include cesium iodide and cesium bromide.

In addition, activators for these scintillators include sodium and thallium.

A support 11 in FIG. 1 can employ not only a polyethylene-based resin but also a resin such as an acrylic resin, a phenol resin, a vinyl chloride resin, a polypropylene resin, a polycarbonate resin and a cellulosic resin, as its material.

In addition, an electromagnetic shield 12 can employ not only aluminum but also a metal such as silver, a silver alloy, copper and gold, as its material.

Furthermore, a protection film 13 has only to be made from a thermoplastic resin, but can be made from a hot melt resin of not only a polyolefin resin but also a polyester-based resin, a polyurethane-based resin and an epoxy-based resin. The hot melt resin is defined as an adhesive resin made from a thermoplastic material which does not contain any of water and a solvent, is solid at a room temperature, and is completely nonvolatile. (Thomas P. Flanagan, *Adhesive Age*, 9, No. 3, 28 (1966)).

Thus, a hot melt resin contains no solvent and no water, and accordingly hardly dissolves a scintillator made from an alkali halide. A scintillator-protecting film using the hot melt resin hardly dissolves the scintillator even in a production process, because of being stacked on a scintillator layer without using a solvent.

A hot melt resin melts when the temperature rises and adheres to a body to be bonded, and when the resin temperature falls, the resin becomes a solid. The adhesive resin layer made of the hot melt resin is different from a solvent-volatilizing and curing type of an adhesive resin layer which is formed by a method of dissolving a thermoplastic resin in a solvent and applying the liquid on the body. The hot melt resin is different also from a chemical reaction type of an adhesive resin which is represented by an epoxy resin and is formed by a chemical reaction.

Hot melt resin materials can be classified mainly into a polyolefin-based resin, a polyester-based resin and a polyamide-based resin. It is important for the protection film 13 to have a high function as a moisture-proof film and transmit visible rays (350 nm to 700 nm) emitted from a scintillator. Hot melt resins having a sufficient moisture-proof function can include polyolefin resins and polyester resins. Particularly, polyolefin resins can be employed because of having a low coefficient of moisture absorption. Polyolefin resins are also suitable because of having high optical transparency.

Accordingly, a polyolefin-based hot melt resin for a protective layer of the scintillator can be used.

The hot melt resin can contain at least one compound selected from the group consisting of an ethylene-acrylic acid copolymer (EAA), an ethylene-acrylate copolymer (EMA), an ethylene-methacrylic acid copolymer (EMAA), an ethylene-methacrylate copolymer (EMMA) and an ionomer resin, as a main component.

Additives to be added to an adhesive include, for instance, a tackifier and a softener.

Tackifiers include: a natural resin such as rosin, polymerized rosin, hydrogenated rosin and a rosin ester; a modified product thereof; an aliphatic compound; an alicyclic compound; an aromatic compound; a petroleum resin; a terpene resin; a terpene-phenolic resin; a hydrogenated terpene resin and a chroman resin. Softeners, for instance, include: process oil, paraffin oil, castor oil, polybutene and low-molecular-weight polyisoprene.

A copolymer contained in an adhesive layer has a weight average molecular weight of about 5,000 to 1,000,000. An ethylene-acrylic copolymer (EAA) has a structure in which a carboxyl group is contained in a polyethylene structure at random as shown in the following structural formula (I):

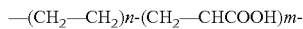

(wherein m and n are positive integers).

In addition, an ethylene-acrylate copolymer is a copolymer of ethylene and acrylate, as is shown in the following structural formula (II):

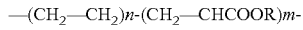

(wherein m and n are positive integers, and R represents $CH_3$, $C_2H_5$ or $C_3H_7$).

In addition, an ethylene-methacrylic copolymer has a structure in which a carboxyl group is contained in a polyethylene structure at random as shown in the following structural formula (III):

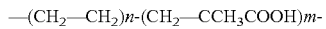

(wherein m and n are positive integers).

Furthermore, an ethylene-methacrylate copolymer has such a structure as is shown in the following structural formula (IV):

(wherein m and n are positive integers, and R represents $CH_3$, $C_2H_5$ or $C_3H_7$).

A protection film 13 contains at least one copolymer among the above described five copolymers or may contain a mixture of two or more of the copolymers. An adhesive layer in the present invention may contain the mixture of the two or more different but similar copolymers, for instance, the mixture of an ethylene-methyl methacrylate copolymer and an ethylene-ethyl methacrylate copolymer.

A melting-starting temperature, melt viscosity and adhesion strength of a hot melt resin for a scintillator-protecting film can be controlled, by mainly appropriately changing the following three elements alone or in combination of two or more: (1) contents of vinyl acetate, acrylic acid, acrylate, methacrylic acid and methacrylic ester in the above described respective copolymers contained in a hot melt resin; (2) a content of the above described copolymer in a hot melt resin; and (3) an additive in a hot melt resin.

A hot melt resin can be used as a scintillator-protecting film in a radiation imaging element for a human body not to aggravate its function as a scintillator-protecting layer, even when sterilizing alcohol has been scattered thereon.

A hot melt resin which is insoluble or slightly soluble in ethyl alcohol can contain an additive such as an adhesion-imparting material in the hot melt resin in an amount of 20% or less, and particularly in an amount of 10% or less.

Figure 10:
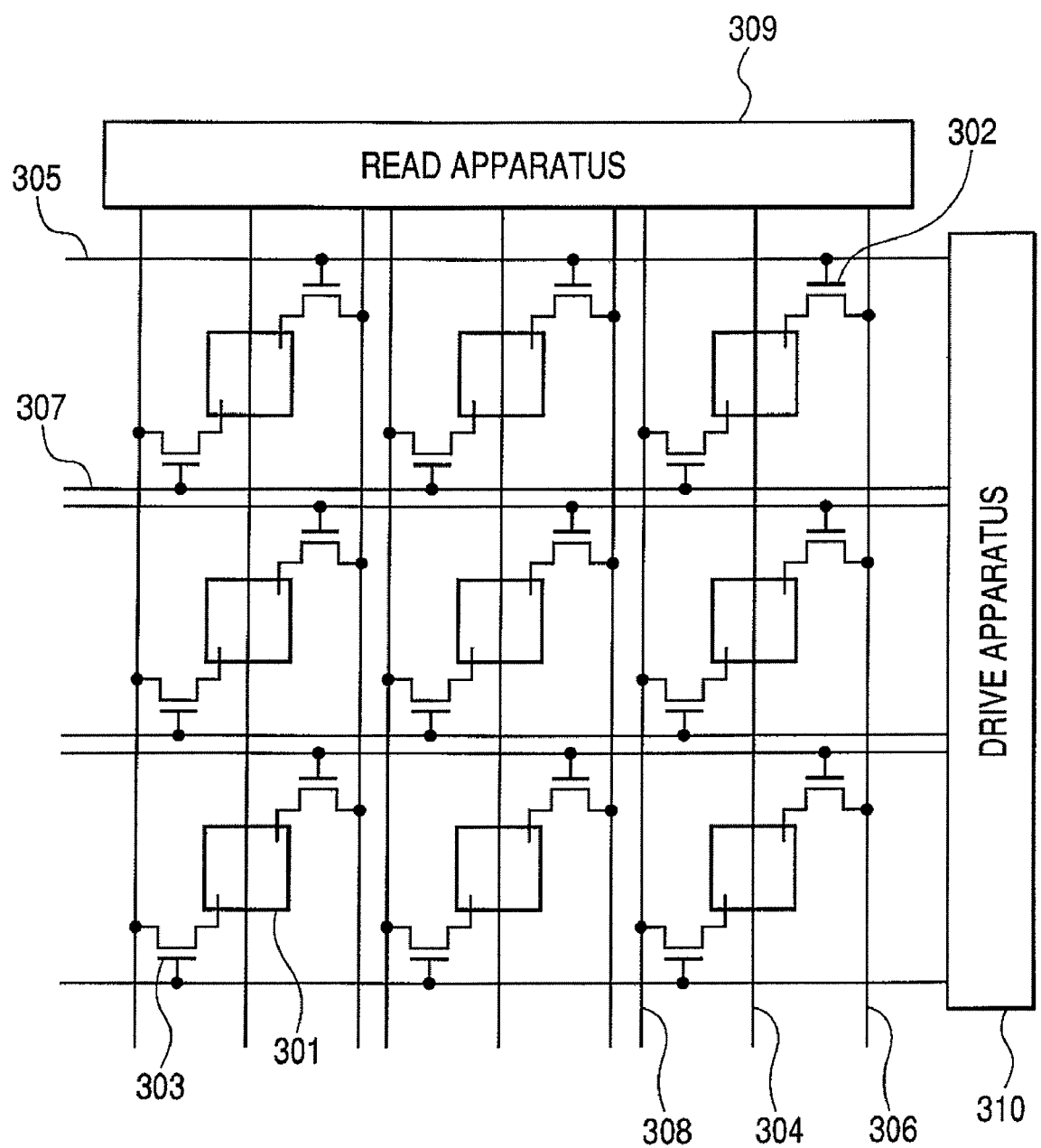
FIG. 10 is an equivalent circuit diagram showing a photoelectric conversion element array according to the first embodiment of the present invention.

In the next place, a photoelectric conversion element array having pixels including a photo sensor and a TFT two-dimensionally formed thereon will be described with reference to an equivalent circuit diagram in FIG. 10. In FIG. 10, a photoelectric conversion element 301, a transfer-switching element 302 and a resetting switch element 303 are two-dimensionally arranged. At first, a bias is given on one electrode of a photoelectric conversion element 101 through a bias wiring 304. In this state, X-rays projected toward an object pass through the object while being damped, and irradiate a scintillator arranged on a photoelectric conversion element 301. Then, the scintillator converts the X-rays to light such as visible light. The light is incident on the photoelectric conversion element 301 and is converted to electrical charge. The electrical charge is transferred to a signal wire 306 by making a drive apparatus 310 apply a gate-driving pulse to a gate wire 305 to control a transfer-switching element 302 into a conductive state, and is read to the outside by a read apparatus 309. Subsequently, a resetting switch element 303 is converted into the conductive state by making the drive apparatus 310 apply the gate-driving pulse to a gate wire 307. Meanwhile, a bias for resetting the photoelectric conversion element is applied to a resetting wire 308, and a residual charge which has been generated in the photoelectric conversion element 301 but has not been all transferred is removed.

Picture signals for one image are obtained by repeating the above-described operation, and an image is obtained by further repeatedly acquiring the picture signals for another image. FIG. 10 shows 3×3 pixels, but practically more pixels such as 2,000×2,000 pixels are arranged on an insulation substrate to compose a radiation detecting apparatus. In addition, a resetting switch element is not necessarily provided.

A photoelectric conversion element array used in the present embodiment has a TFT and a photoelectric conversion element formed on a glass substrate so as to be aligned on the same plane. However, a photoelectric conversion element array can also be used which has a configuration having a switching element such as a TFT formed on the glass substrate, a medium of an insulation layer, and a photoelectric conversion element formed thereon. Even the photoelectric conversion element array with such a configuration has two types. One is a configuration in which a photoelectric conversion layer (semiconductor layer) of the photoelectric conversion element is not stacked on a TFT so that a defective region produced in the TFT can be repaired by using a laser beam. The other is a configuration in which the photoelectric conversion layer (semiconductor layer) of the photoelectric conversion element is stacked even on the TFT to increase an aperture ratio.

The present embodiment can impart a scintillator layer in itself a moisture-proof function by increasing Tl concentration in the perimeter of the scintillator layer for the purpose of further enhancing the reliability for a moisture-proof effect, though the moisture-proof effect can be obtained only by a single moisture-proof protective layer of a hot melt resin.

Thereby, a radiation detecting apparatus having higher reliability at a low cost can be accomplished, because there is no need to add a mechanism for protecting a scintillator layer, so that steps and materials can be reduced.

In the present embodiment, a thermoplastic resin layer is used as a moisture-proof protective layer for a scintillator layer, but this layer is not limited to the use of a thermoplastic resin. Any material can be used as long as it has a moisture-proof effect and an adhesive function. For instance, a sticky material is also acceptable.

Figure 7:
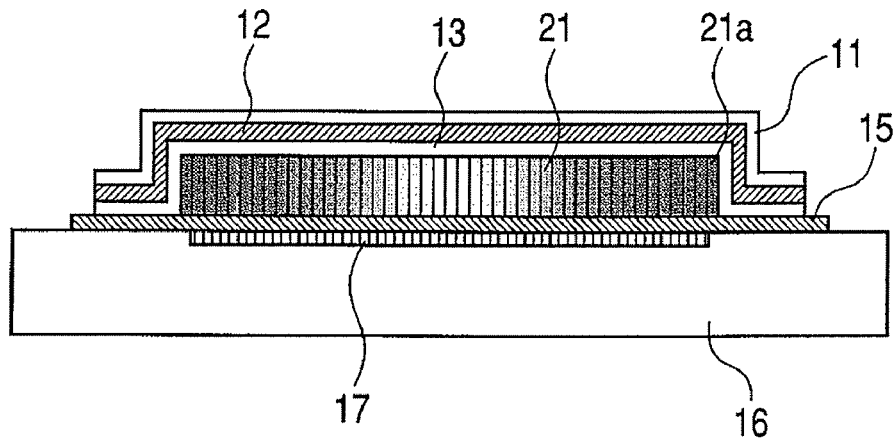
FIG. 7 is a sectional view showing another configuration example of a radiation detecting apparatus according to the first embodiment of the present invention.

In the above described example, the Tl concentration approximately concentrically and isotropically changes from the center to a peripheral area, as is shown in FIG. 1. The present embodiment can employ not only such concentration distribution as is shown in FIG. 7, but also a concentration distribution in which a region 21a with a high TlI concentration is arranged only in a peripheral end within a scintillator layer. FIG. 7 is a sectional view of a radiation detecting apparatus. In FIG. 7, only the black region 21a in the peripheral end of the scintillator layer 21 has a high Tl concentration. In this case, it is acceptable that the Tl concentration is uniform within a concentric circle and the Tl concentration is higher outside the concentric circle. In addition, the concentration distribution is not limited to a concentric circle shape, but may be a frame shape in which the peripheral area has a frame shape and high Tl concentration, and the inner part inside the frame part has a uniform Tl concentration.

The scintillator layer having a uniform Tl concentration in a part other than the peripheral area can also show uniform characteristics such as a quantity of light emission and sharpness. In other words, an example as shown in FIG. 7 can have uniform characteristics in a part other than the peripheral end, while reliably imparting a moisture-proof effect to a scintillator in itself.

Second Embodiment

Figure 8:
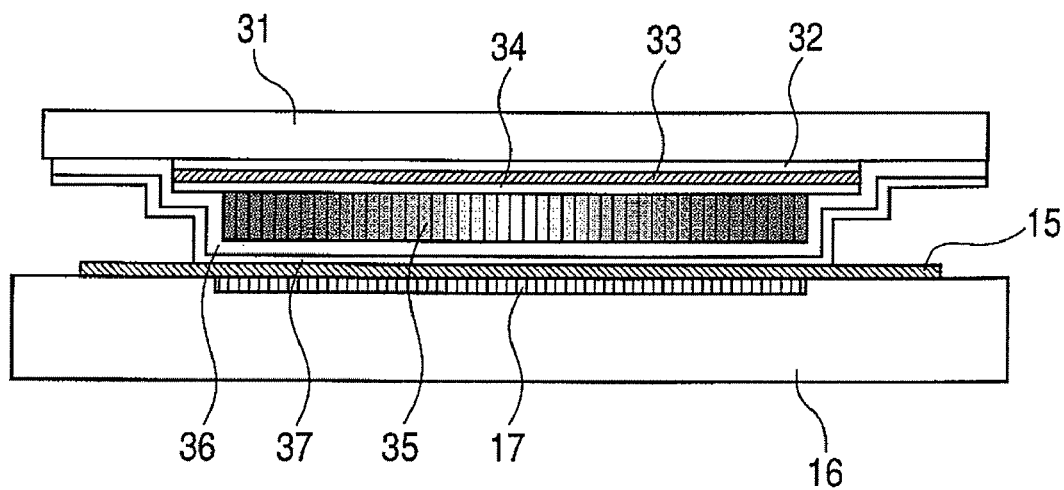
FIG. 8 shows a sectional view of a radiation detecting apparatus according to the second embodiment of the present invention.

FIG. 8 shows a sectional view of a radiation detecting apparatus according to the second embodiment of the present invention. In the present embodiment, the radiation detecting apparatus is composed by laminating a scintillator panel with a sensor panel through an adhesive.

The scintillator panel is produced by forming a scintillator layer on a base plate which allows X-rays to pass through itself as amorphous carbon does, with a vapor-deposition technique. The used sensor panel has an insulation layer 15 formed on a glass substrate 16 having a photoelectric conversion element array 17 formed thereon, as is shown in FIG. 1. The radiation detecting apparatus is produced by bonding the surface of the scintillator panel in a reverse side to the base plate, with the sensor panel having a photoelectric conversion element formed thereon, by using an adhesive.

In FIG. 8, reference numeral 31 denotes a base plate made from amorphous carbon, reference numeral 32 denotes an insulation layer, reference numeral 33 denotes an Al layer for reflecting light, reference numeral 34 denotes an insulation layer, and reference numeral 35 denotes a scintillator layer made from CsI and TlI. In addition, reference numeral 36 denotes a thermoplastic resin which is a moisture-proof protective layer, and reference numeral 37 denotes a polyethylene terephthalate resin layer which allows light to pass through it.

A concentration distribution of Tl and a method of adding Tl are omitted because of being similar to the case which was described in the first embodiment with reference to FIGS. 1, 2A, 2B, 3, 4, 5 and 6.

It goes without saying that an effect equal to that in the first embodiment is obtained in the present embodiment as well. In addition, the present embodiment can confirm the characteristics by using a single scintillator panel alone. The radiation detecting apparatus according to the present embodiment can be manufactured with an enhanced yield, because when the scintillator panel or the sensor panel has a defect, it can be eliminated before being laminated.

Figure 9:
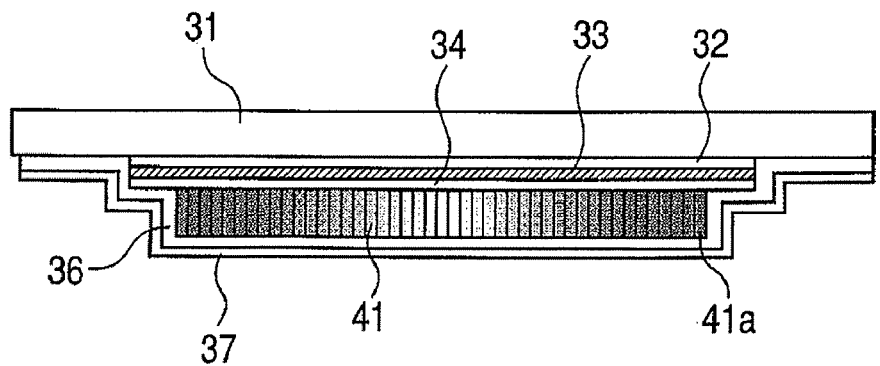
FIG. 9 is a sectional view showing another configuration example according to the second embodiment of the present invention.

FIG. 9 shows another example of a configuration according to the present embodiment. The configuration example in FIG. 9 employs the configuration shown in FIG. 7 as a scintillator panel. Specifically, a scintillator layer 41 has a higher Tl concentration only in a peripheral end 41a. It goes without saying that the configuration example also shows the same effect as in the case of the first embodiment described with reference to FIG. 7.

Third Embodiment

Figure 11:
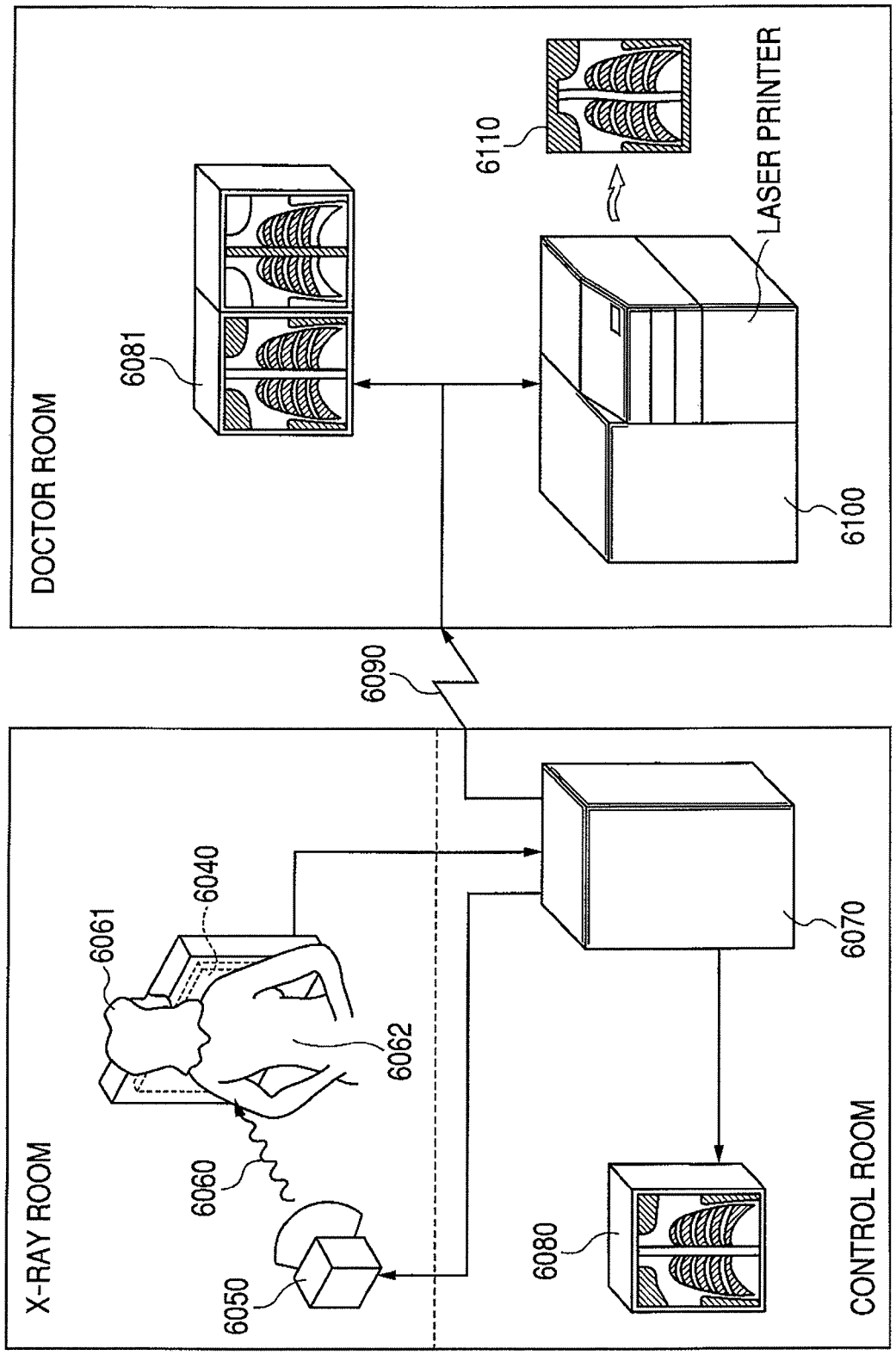
FIG. 11 is a view showing an example in which a radiation detecting apparatus according to the present invention is applied as a radiation detecting system.

FIG. 11 is a view showing an example in which a radiation detecting apparatus according to the present invention is applied as a radiation detecting system. The radiation detecting apparatus is the radiation detecting apparatus in the above described respective embodiments.

As shown in FIG. 11, X-rays 6060 generated in an X-ray tube 6050 of a radiation source pass through the thorax 6062 of a patient or subject 6061, and is incident on a radiation detecting apparatus 6040 for taking a radiation image. The incident X-rays include information about the interior of the body of the patient 6061. A scintillator in the radiation detecting apparatus 6040 emits light in response to incident X-rays, and the light is photoelectrically converted to electric information. The information is converted into digital signals. The digital signals are image-processed into an image by an image processor 6070 of a signal processing unit. Then, the image can be observed through a display 6080 of a display unit in a control room.

The information can be also transferred to a remote place through a transfer unit such as a telephone line 6090, and can be displayed on a display 6081 of the display unit arranged in a doctor's office located elsewhere, or can be saved in a recording unit such as an optical disk. Thereby, a doctor at a remote place can examine the patient. The information can be recorded in a film 6110 of a recording medium by using a film processor 6100 of a recording unit.

As many apparently widely different embodiments of the present invention can be made without departing from the spirit and scope thereof, it is to be understood that the invention is not limited to the specific embodiments thereof except as defined in the claims.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2006-056473, filed Mar. 2, 2006, which is hereby incorporated by reference herein in its entirety.

What is claimed is:

1. A radiation detecting apparatus comprising:
a sensor panel that has a substrate, and has a plurality of pixels each of which has a photoelectric conversion element for converting light into an electric signal, arranged on the substrate; and
a scintillator layer arranged over the pixels, wherein the scintillator layer has a columnar crystal structure including a plurality of columnar crystals, and the scintillator layer contains cesium iodide as a main ingredient and thallium as an activator such that a concentration of the thallium in a peripheral area of the scintillator layer is higher than a concentration of the thallium in a central area of the scintillator layer, and such that the concentration of the thallium in the peripheral area of the scintillator layer is 1.0 mol % or more with respect to the concentration of cesium iodide, and the concentration of the thallium in a central part of the scintillator is 0.5 mol % or more but 1.5 mol % or less with respect to the concentration of cesium iodide; and
a metal layer covering the scintillator layer.

2. The radiation detecting apparatus according to claim 1, wherein the average concentration of the activator in the outside of the region in the scintillator layer, which faces a region having the pixels formed therein, is higher than the average concentration in the region which faces the region having the pixels formed therein.

3. The radiation detecting apparatus according to claim 1, wherein the concentration of the activator isotropically increases from the central part in a plane of the scintillator layer to the peripheral area.

4. The radiation detecting apparatus according to claim 1, wherein the concentration of the activator in the peripheral area of the scintillator layer is higher than the concentration of the activator in all other areas of the scintillator layer.

5. The radiation detecting apparatus according to claim 1, wherein the scintillator layer is arranged on the substrate to compose a scintillator panel, and the scintillator panel is laminated to the sensor panel.

6. A radiation detecting system comprising:
the radiation detecting apparatus according to claim 1;
a signal processing unit for processing a signal sent from the radiation detecting apparatus;
a recording unit for recording the signal sent from the signal processing unit;
a display unit for displaying the signal sent from the signal processing unit;
a transfer processing unit for transferring the signal sent from the signal processing unit; and
a radiation source for generating the radiation.

* * * * *